United States Patent [19]

Holman et al.

[11] 4,230,118
[45] Oct. 28, 1980

[54] AUTOMATIC LANCET

[76] Inventors: Rury R. Holman, 42 Meadow Close, Farmoor; Robert C. Turner, May Cottage, Great Milton, both of England

[21] Appl. No.: 931,154
[22] Filed: Aug. 4, 1978

[30] Foreign Application Priority Data

Aug. 5, 1977 [GB] United Kingdom ............... 33029/77

[51] Int. Cl.² .............................................. A61B 17/34
[52] U.S. Cl. .................... 128/314; 128/329 R
[58] Field of Search ................. 128/314, 315, 329 R, 128/637, 305; 30/366, 272 R; 74/64

[56] References Cited

U.S. PATENT DOCUMENTS

| 6,288 | 4/1849 | Johnson | 128/314 |
| 16,478 | 1/1857 | Gordon | 128/314 |
| 16,479 | 1/1857 | Gordon | 128/314 |
| 55,620 | 6/1866 | Capewell | 128/314 |
| 2,646,799 | 7/1953 | Jacoby | 128/314 |

FOREIGN PATENT DOCUMENTS

| 5612 of 1828 | United Kingdom | 128/314 |
| 1279936 6/1972 | United Kingdom | 128/314 |

Primary Examiner—William E. Kamm
Assistant Examiner—Michael H. Thaler
Attorney, Agent, or Firm—Cushman, Darby & Cushman

[57] ABSTRACT

An automatic lancet device for use in pricking a patient's skin to yield a blood sample. The device comprises an arm pivoted at one end in a housing and protruding therefrom at its other end through an arcuate slot in the housing, the outer end of the arm being formed outside the housing as a carrier which will hold a replaceable mounted needle with its point projecting tangentially. The arm is spring-biassed in the angular direction corresponding to the direction in which the needle points, and can be held retracted against the spring means by a latch in the housing. When the latch is released the arm is swung forwardly by the spring means to effect a pricking operation. The spring is arranged to be slightly over-center with respect to the arm pivot when the arm is fully forward, to assist the recoil of the arm. A detachable finger rest is mounted in the housing, and includes a ring for resting on the patient's skin, so that the needle projects through the ring for pricking.

7 Claims, 7 Drawing Figures

AUTOMATIC LANCET

FIELD AND BACKGROUND OF THE INVENTION

This invention relates to a lancet device for use in taking skin capillary blood samples.

In the case of certain diseases such as diabetes, the patient is required to provide regular small specimens of blood, which are sent for analysis in a specially designed carrier tube. This involves pricking a finger or other suitable part of the anatomy in order to obtain the blood specimen. It is physically and psychologically difficult for many people to prick their own finger with a hand-held needle, which must be sterile, and an object of the invention is to provide a simple hand-held automatic lancet device to facilitate this task.

SUMMARY OF THE INVENTION

According to the present invention, a lancet device comprises a movable arm pivoted in a housing for rotation through a limited angle and having at one end remote from its pivot a holder adapted to receive a replaceable mounted needle and to hold the needle by its mounting pointing in the tangential direction, spring means acting on the arm to bias it for rotary movement about its pivot from a retracted position into an operative position with the point of the needle exposed and projecting forwardly for pricking, and releasable latch means for holding the arm and its needle in the retracted position against the force of the spring means, whereby on release of the latch by means of a manually-operable trigger the arm will be urged forwardly by the spring means towards its operative position to perform a pricking operation.

A part of the arm, or a member secured thereto, may protrude from the housing to enable the device to be manually reset. For example the housing may have an arcuate edge concentric with the pivot of the arm, through a slot in which edge the outer end portion of the arm protrudes to hold the mounted needle just outside the arcuate edge for easy removal and replacement of the mounted needle.

The arm may be arranged to rebound or recoil slightly from its operative position, so that the tip of the needle is automatically retracted from the patient's skin after a pricking operation. A suitable buffer may be provided for this purpose.

Alternatively or in addition the spring means may be arranged so that the angular direction of bias of the spring means reverses when the arm reaches a neutral position shortly before its operative position, so that the arm will be carried by its own inertia past the neutral position against the action of the spring means into the operative position from which it will then tend to be retracted back into the neutral position. For example the spring may comprise a tension spring acting on a point of the arm radially offset from the pivot axis, and being arranged to assume a dead-centre position in alignment with the pivot axis when the arm reaches its neutral position.

A removable throw-away finger rest may be provided on the housing and protruding therefrom for resting on the patient's finger to indicate the approximate position in which the needle will prick when the latch is released. The protruding portion of the finger rest may be formed as a ring through which the point of the needle projects to perform a pricking operation when the arm reaches its operative position. The finger rest should be readily removable for disposal after use, when it will be replaced by a sterile replacement.

The invention provides a simple device whereby a patient may prick his own finger, holding the device in one hand and placing it against a finger of the other hand before releasing the trigger of the latch. It provides for the mounted needle to be easily removed for sterilisation or disposal after each operation and replaced by a sterile needle, and by virtue of the rotary operative movement of the arm carrying the needle the device avoids the danger inherent in a spring-loaded linear plunger-type lancet device which a child could use as a toy "gun" to project pointed missiles.

BRIEF DESCRIPTION OF THE DRAWINGS

The invention may be carried into practice in various ways, but one specific embodiment thereof will now be described by way of example only and with reference to the accompanying drawings, in which.

DESCRIPTION OF THE PREFERRED EMBODIMENT

Figure 1:
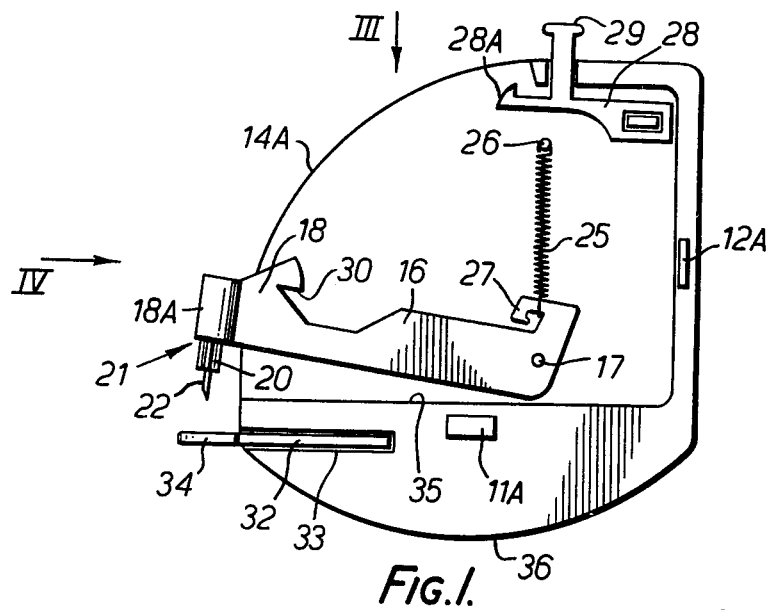
FIG. 1 is a plan of a lancet device with the cover portion of its housing removed and with a needle 21 fitted.
Figures 2, 4:
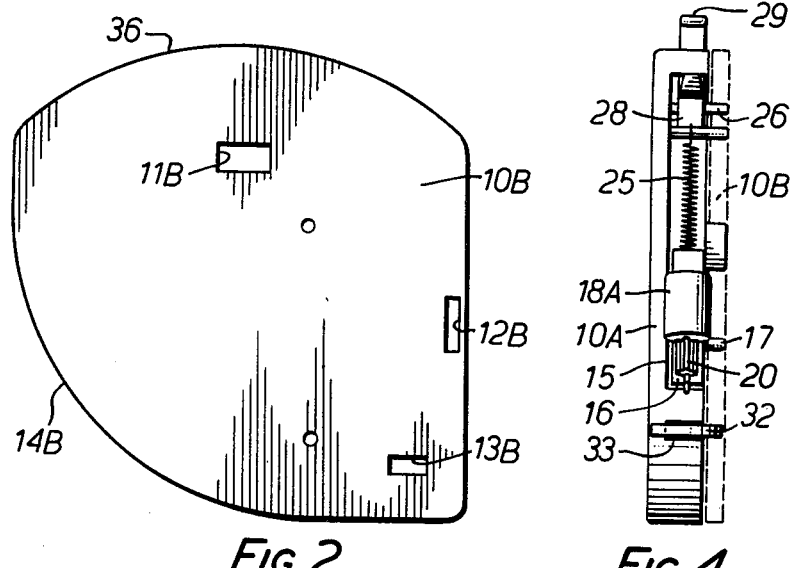
FIG. 2 is a plan of the housing cover portion showing its interior side.
FIGS. 3 and 4 are respectively side and end elevations of the device of FIG. 1 as seen in the direction of the arrows III and IV.
Figure 3:
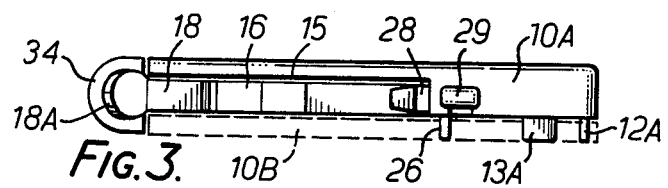

The illustrated embodiment comprises a two-part housing of generally quadrant shape having a base portion 10A and a separate detachable cover portion 10B, which can be mutually located by means of co-operating inter-engageable formations 11A, 11B, 12A, 12B and 13A 13B and held together by screws (not shown), or by other means such as adhesive or welding or heat-sealing of plastic. The two housing portions 10A and 10B have arcuate edges 14A, 14B between which a slot 15 is defined when the housing is closed, and an arm 16 is pivotally mounted at its inner end in the housing by means of a pivot pin 17, and protrudes at its outer end 18 through the slot 15. The axis of the pivot pin 17 is concentric with the edges 14A, 14B.

At its outer end 18 the arm has a holder 18A in the form of a cylinder with a bore opening through its lower end, which can receive and hold the ribbed mounting 20 of a mounted needle 21, to hold the needle with its pointed tip 22 projecting generally tangentially with respect to the edges 14A, 14B and the pivot pin 17.

A helical tension spring 25 extends between an anchorage pin 26 on the housing portion 10A and a hook 27 formed on the arm 16 near its pivoted end, the hook 27 being radially-offset from the pivot pin 17. In the position of the arm shown in FIG. 1 the spring 25 is directly aligned with the pivot pin 17 so that it exerts no turning torque on the arm 16. The position of the arm 16 in FIG. 1 is thus a neutral or dead-centre position. When the arm is rotated in the clockwise direction in FIG. 1 to the other end of the slot 15, the spring 25 will be extended and will exert a resilient torque on the arm 16 tending to turn the arm towards its neutral position. A resilient latch member 28 with a latch hook 28A and an operating trigger 29 is mounted in the housing member 10A to co-operate with a detent recess 30 formed in the arm 16 to latch the arm in its retracted position. Pressure on the trigger 29 will release the latch to allow the spring 25 to rotate the arm in the anti-clockwise direction in FIG. 1 back to its neutral position. The inertia of the swinging arm will carry it through its neutral position for a pricking operation as will now be described.

A replaceable finger rest 32 is detachably mounted in a slot 33 in the housing portion 10A and has a ring 34 formed at its outer end to protrude from the housing. The swinging arm after overrunning its neutral position will reach its limiting, operative position in which it engages a step 35 in the housing portion 10A which acts as a buffer at the end of the slot 15, and the tip of the needle will then project through the ring 34 to perform a pricking operation. The rotation of the arm will be checked by the engagement of the arm with the step 35, and the arm will then be returned to its neutral position by the return torque exerted by the overcentre spring 25, thus retracting the needle to a position with its tip behind and guarded by the ring 34.

Figure 5:
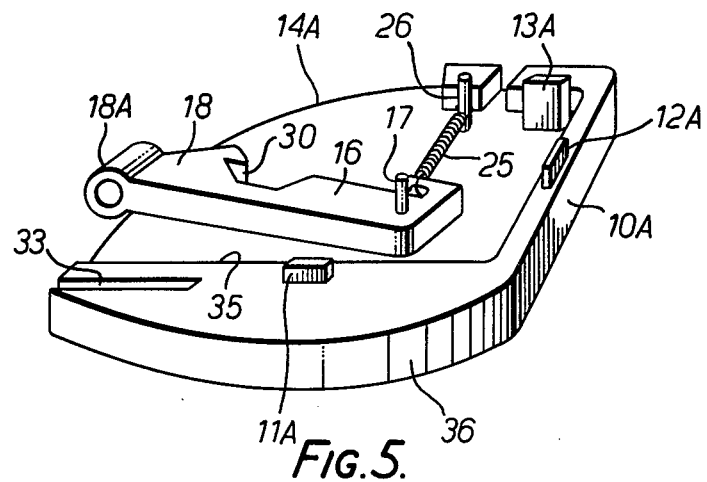
FIG. 5 is a perspective view of the device with the cover removed.
Figure 6:
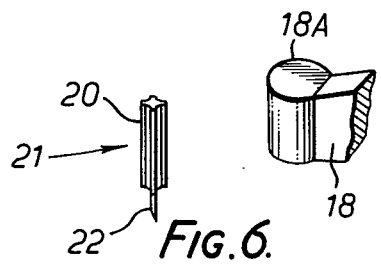
FIG. 6 shows separately a mounted needle, and the holder for it formed at the outer end of the pivoted arm of the device.

The latch 28, the needle 21 and the finger rest 32 are omitted from FIG. 5 for the sake of clarity.

Figure 7:
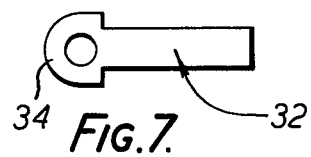
FIG. 7 shows separately the replaceable finger rest of the device.

The finger rest 32 may be an inexpensive moulding of polythene or other flexible plastics material, whose profile is shown in FIG. 7.

Thus to operate the pricker device, the user will fit a new sterile needle 21 in the holder 18A with its needle point 22 directed towards the guard ring, and will fit a new sterile finger rest in the slot 33. He will then set the device by turning the arm back into its retracted position where it will be held by engagement with the latch 28. He will then, holding the set device in one hand, place the finger rest ring 34 over the pulp of a finger of the other hand from which he wishes to draw a blood sample, resting that finger on the curved base 36 of the housing, and will then press the trigger 29 to release the latch. The arm 16 and needle 21 will fly forward under the force of the spring 25, turning about the pivot 17, and travelling through the neutral position until the arm is checked by the step at the end of the slot 15 at which time the tip of the needle is projected through the centre of the finger rest ring 34 to prick the patient's skin below. The arm will rebound from its limiting operative position back into its neutral position, aided by the return force of the over-centre spring 25, retracting the tip of the needle from the patient's skin to a position behind the ring 34. The used needle 21 and the finger rest 32 can now be removed and thrown away or re-sterilised, and a sterile replacement needle 21 and finger rest 32 can be fitted into the holder 18A and slot 33 for re-use.

The lancet device can also be used for blood sampling from other sites, e.g. the ear lobe or heel prick.

The whole device is simple, light in weight and inexpensive to manufacture, and can be mass-produced by injection-moulding of its main parts from a suitable plastics material.

What we claim as our invention and desire to secure by Letters Patent is:

1. A lancet device which comprises:
   a housing;
   a movable arm pivoted in the housing for rotation about a pivot therein through a limited angle;
   a holder at one end of the arm remote from the pivot, the holder being adapted to receive a replaceable mounted lancet needle and to hold the latter by its mounting pointing in the tangential direction;
   spring means acting on the arm to bias it angularly for rotation about its pivot from a retracted position towards an operative position in which the point of a mounted lancet needle carried in the holder will be exposed projecting forwardly for a pricking operation; and
   releasable latch means for holding the arm in the said retracted position against the force of the said spring means;
   said latch means including a manually-operable trigger for releasing said latch means, whereby on release of said latch means the arm will be urged forwardly by said spring means to rotate into its operative position to perform a pricking operation;
   said spring means having a characteristic such that the resultant biasing torque which it exerts on the arm reduces progressively in magnitude as the arm rotates from its retracted position towards its operative position until the arm reaches a neutral position shortly before its operative position, the resultant biasing torque reaching zero in said neutral position of the arm and thereafter reversing in angular direction to increase progressively as the arm is carried by inertia towards its operative position against the reversed biasing torque, whereby the said spring means will tend to retract the arm from its operative position towards and into its neutral position so that the tip of the needle is automatically withdrawn after a pricking operation.

2. A lancet device as claimed in claim 1 in which a portion of the arm remote from the pivot protrudes from the housing to enable the device to be manually reset.

3. A lancet device as claimed in claim 2, in which the housing has an arcuate edge concentric with the pivot of the arm, and a slot in said edge, through which slot the said portion of the arm protrudes, the holder being at the outer end of said portion whereby a mounted needle will be held by the holder just outside the arcuate edge for easy removal and replacement of the needle.

4. A lancet device as claimed in claim 1, which includes a removable throw-away finger rest provided on the housing and protruding therefrom for resting on a patient's finger to indicate the approximate position in which the needle will prick when the latch is released.

5. A lancet device as claimed in claim 4, in which the protruding position of the finger rest is formed as a ring through which the point of the needle projects to perform a pricking operation when the arm reaches its operative position.

6. A lancet device as claimed in claim 1 in which said spring means comprises a tension spring acting on the arm at a point radially offset from said pivot, the tension spring being arranged to assume a dead-centre position in alignment with said pivot when the arm is in the said neutral position shortly before its said operative position whereby the angular direction of bias of said tension spring on the arm is arranged to reverse as the arm passes through the said neutral position.

7. A lancet device which comprises a housing, a movable arm pivoted in the housing for rotation about a pivot therein through a limited angle, a holder at one end of the arm remote from the pivot, holder being adapted to receive a replaceable mounted needle and to hold the needle by its mounting pointing in the tangential direction, spring means acting on the arm to bias it for rotary movement about its pivot from a retracted position into an operative position in which the point of a mounted needle carried in the holder will be exposed and projecting forwardly for pricking, and releasable latch means for holding the arm in the retracted position against the force of the spring means, whereby on release of the latch by means of a manually-operable trigger the arm will be urged forwardly by the spring means towards its operative position to perform a pricking operation, the arm being arranged to rebound or recoil slightly from its operative position so that the tip of the needle is automatically retracted after a pricking operation; the spring means acting on the arm with an angular direction of bias on the arm which is arranged to reverse when the arm reaches a neutral position shortly before its operative position, so that the arm will be carried by its own inertia past the neutral position against the action of the spring means into the operative position from which it will then tend to be retracted back into the neutral position;

the spring means comprising a tension spring acting on a point of the arm radially offset from the pivot, and in alignment with the pivot when the arm reaches its neutral position.

* * * * *